United States Patent [19]
Tortal et al.

[11] Patent Number: 5,833,685
[45] Date of Patent: Nov. 10, 1998

[54] CRYOSURGICAL TECHNIQUE AND DEVICES

[76] Inventors: Proserfina R. Tortal; Grace Tortal-Quirong; Rolando A. Quirong; Eleazar R. Tortal; Jocelyn Fonacier Tortal, all of P.O. Box 291541, Los Angeles, Calif. 90029

[21] Appl. No.: 528,921

[22] Filed: Sep. 15, 1995

Related U.S. Application Data

[63] Continuation-in-part of Ser. No. 212,992, Mar. 15, 1994, abandoned.

[51] Int. Cl.$^6$ ...................................................... A61B 17/32
[52] U.S. Cl. ................................ 606/23; 606/21; 606/25
[58] Field of Search ........................ 606/20–26; 607/104, 607/105

[56] References Cited

U.S. PATENT DOCUMENTS

| | | |
|---|---|---|
| 3,298,371 | 1/1967 | Lee . |
| 3,421,508 | 1/1969 | Nestrock . |
| 3,948,269 | 4/1976 | Zimmer . |
| 4,275,734 | 6/1981 | Mitchiner . |
| 5,108,390 | 4/1992 | Potocky et al. . |
| 5,254,116 | 10/1993 | Baust et al. . |

FOREIGN PATENT DOCUMENTS

| | | |
|---|---|---|
| 2236253 | 4/1991 | United Kingdom . |

*Primary Examiner*—Michael Peffley

[57] ABSTRACT

Devices and method for freezing of tissues. Devices comprise a cryosurgical probe that can be very slim with diameter up to a fraction of a millimeter for very focal freezing application, and an insulating canula for adjusting freeze zone. A cryosurgical probe with solid and liquid cold sources, wherein the solid cold source forms the portion of the probe inserted to tissue for thermal exchange while the liquid cold source maintains the operating temperature of said solid cold source. Method for rupturing targeted cells during freezing while minimizing freezing of nearby tissues and vasculatures.

14 Claims, 5 Drawing Sheets

CRYOSURGICAL TECHNIQUE AND DEVICES

CROSS REFERENCE TO RELATED APPLICATIONS

This patent application Ser. No. 08/528,921 is a CIP of Ser. No. 08/212,992 filed Mar. 15, 1994 (now abandoned), Small Entity.

RIGHTS TO INVENTIONS MADE UNDER FEDERALLY-SPONSORED RESEARCH AND DEVELOPMENT

None

FIELD OF THE INVENTION

This invention relates to a probe and technique for freezing of tissues.

Probes for freezing of live tissues vary with the nature of cold source and means for maintaining their operating temperature.

Cold source can be in the form of coolant gas such as Freon gas, carbon dioxide or nitrous oxide, etc., as discussed by R. Mitchiner in U.S. Pat. No. 4,275,734, or most recently, liquid nitrogen.

Usual liquid nitrogen probes consist of a hollow tubing wherein the supply liquid pass through up to the close end tip in contact with the tissue being frozen. The tip portion is usually made up of thermoconductive material such as stainless steel as the rest of the probe or of a "thin polymer" as anticipated by Mackay and Hossak (UK Pat GB 2 236 253 A). Walls are provided with insulation, such as having an inner and outer wall separated by a vacuum chamber or lined with polycarbon materials, e.g., polyurethane or polyethylene materials. Nestrock (U.S. Pat. No. 3,421,500) uses a disposable smooth hollow plastic tip-end, as of a molded styrene or polyethylene. Other insulation materials is in the form of foam plastic filling as mentioned by Nestrock.

As liquid nitrogen travels to the tip, it absorbs heat from the wall of the probe by thermal conduction. Liquid nitrogen evaporates more easily if the wall of the probe is not precooled. Smaller diameter probes provide greater frictional heat to the flowing liquid nitrogen as described in Jacob and McAdams' equation:

$$l = Lvc_v r/3;$$

where l=thermal conductivity (watts/cm°K)

Describes thermal conduction between the walls of the probe and the nitrogen fluid;

L=mean free path (cm) Includes the probe's diameter;

v=velocity (cm/s);

$c_v$=specific heat of liquid nitrogen at constant volume (J/g°K);

r=density (gm/cm$^3$)

Thus, smaller diameter probes pose limitations to highly volatile liquid nitrogen. Liquid nitrogen probes can not therefore be of very slim probes.

When liquid nitrogen reaches the tip of the probe, it absorbs heat from the tissue in contact and vaporizes. The volume of liquid nitrogen increases 700 times as it vaporizes into gas. Nitrogen has lower heat transfer coefficient at gas state than at liquid. These two factors involving volume and state transformation of nitrogen are the causes of inadequate freezing of targeted tissues. Studies show that it is necessary that a probe be able to cool a target tissue up to −40° C. to assure cellular freezing. This is because, water migrates from cells to vasculatures. With more water in nearby vessels and interstices, they become the more favorable site for ice formation. Such that during freezing treatment, the vessels and interstices freeze faster that the targeted tissue. As ice is being formed within these vessels, electrolytes and other fluids within them are excluded. This creates hyperosmotic condition within these vessels, drawing out more water from cells and dehydrating the cells. With the targeted cells being dehydrated, less ice is formed within them. Cellular bursting which is cause by water expanding in volume within a cell as it turns into ice is not likely to happen within a dehydrated cell. This is how nature prevents further damage to cells during freezing.

With these complications, various features and methods were added in later probes: Walls are precooled prior to actual freezing by spraying it with liquid nitrogen. Vapors formed are cooled down by means of Joule-Thompson effect wherein the tip of the probe has expanding chamber to lower the vapor pressure and thus lower its temperature, e.g. in Potocky et al in U.S. Pat. No. 5,108,390 and Baust et al in U.S. Pat. No. 5,254,116. An exhaust chamber to collect vaporized liquid nitrogen at the tip as in Baust et al version.

The focus of the above-mentioned probes is on keeping the temperature of liquid nitrogen as low as possible, below the liquid nitrogen's critical temperature (boiling point=−196.15° C.) for fast freezing of targeted tissue. However, effective freezing of tissues is not only dependent on the efficiency of probes to cool tissues but also on their water content. With more water inside the targeted tissues, bigger ice crystals that produce greater cellular strain would be formed. With maximum amount of water within targeted cells, cellular bursting which guarantees cellular death is more likely to happen.

A method for hastening ice formation within targeted cells was done by Aaron Hed. The flexible probe designed by Aaron Hed (U.S. Pat. No. 5,139,496) for freezing of small selected location is accompanied by a method of sending out low power ultrasound to targeted tissue. Ultrasound wave forms artificial nucleation within targeted cells and ice would begin to form prior to achieving the nucleation temperature (temperature wherein ice normally begins to form within the cells~−0.8° C.). However, in this method there is still left a competition between intracellular freezing (within cells) and interstitial freezing (outside cells). While nucleation is initiated within cell to cause ice formation, water-filled interstices and nearby vascular region remain the favorable site for ice formation. Since growth of ice creates hyperosmotic condition, water is drawn by both the cells and the interstices or nearby vascular tissue as both have ice formed within. Moreover, since nucleation is initiated during slow freezing there is time for water to migrate to vascular area before nucleation.

Although the discussed probes having means to lessen and extract nitrogen vapors, and method of initiating cellular freezing have enabled rapid freezing of targeted tissue prior to its cellular dehydration, freezing does not result to cellular bursting. Thus, for effective cellular bursting, it is necessary to maintain maximum amount of water within targeted cells and freeze them at a rate faster than the migration of water from cells to vessels.

Thus, it is the object of this invention to maximize the probability of cellular rupture during freezing which is the most effective way to destroy targeted tissue. It is also the object of this invention to minimize the freezing of nearby tissues outside the target area.

It is also the object of this invention to eliminate the complications on gas blockage associated in liquid nitrogen probes which results into poor freezing.

It is also the object of this invention to extend the capability of cryosurgical probes to be of very slim probes, with diameter up to a fraction of a millimeter for very focal freezing applications.

SUMMARY OF THE INVENTION

The above objects are achieved by means of devices and method described below:

A Cryosurgical Probe and Insulating Canula

A cryosurgical probe for freezing of tissues wherein a solid carbon dioxide at −196° C. or below is shaped into a slender rod adaptable for insertion to tissue. The carbon dioxide extends to the handle portion of the probe wherein liquid nitrogen is circulated during freezing to cool down said solid carbon dioxide. Liquid nitrogen is circulated within a thermoconductive parabolic tube, located inside a vacuum walled cylindrical handle. The vertex of said parabolic tube is in contact with the base of said carbon dioxide for heat exchange. A thermoconductive polyester, 0.55 mm. thick serves as a skin casing for said carbon dioxide whose close end tip portion is placed in contact with the targeted tissue for thermal heat exchange. An insulating tube circumscribes portion of the carbon dioxide not part of thermal exchange such as excluding the tip region in contact with the targeted tissue and the base in contact with the parabolic tube. The base of the handle proximal to the vertex of the parabolic tube is equipped with a hole adaptable for bayonet coupling with the insulating tube. Portion of the insulating tube, which includes the protruding base of the carbon dioxide in contact with the vertex of the parabolic tube, pass through the said hole. The other base of the cylindrical handle has two holes through which the inlet and outlet ends of the parabolic tube pass through.

A canula for guiding the insertion of the above mentioned probe is made to consist of polyurethane lined with polyethylene in the inside structure. Said canula serves to adjust the freeze zone, insulating portion of the probe not in contact with the targeted tissue.

Inducing Rupture of Targeted Cells During Freezing

To produce bigger ice crystals within targeted cells that creates greater cellular strain conducive for cellular rupturing, hyperosmotic condition is first induced within targeted tissue prior to its freezing. Mannitol of volume equal to at least 10% of the volume of targeted tissue is injected to targeted tissue. Mannitol elevates the osmotic pressure of the targeted tissue. Ten minutes after the injection of mannitol, water of volume equal to at least 50% of the volume of targeted tissue is injected to same site to bloat targeted cells with water. Freezing by means of a cryosurgical probe follows ten minutes after the injection of water.

DETAILED DISCUSSION OF THE INVENTION

The Solid Cold Source

The present invention utilizes a solid carbon dioxide at temperature between −196° C. to −205° C. to form portion of the probe in contact with tissue instead of pumping liquid nitrogen to the tip of the probe.

The solid carbon dioxide is in the form of slender rod, 2.5 mm. tip diameter or less depending on desired freezing area A length of about 245 millimeter extends from the tip of the probe to the handle portion. A length of about 25 mm. or less (depending on the diameter of the targeted tissue) from the tip portion of the probe forms the freeze zone of the probe.

Carbon dioxide has much higher critical temperature (referring to temperature of "evaporation") than liquid nitrogen. Because of this, production of gas that has lower heat transfer coefficient is eliminated within the present probe. The internal refrigerant characteristic of solid carbon dioxide further enables the present probe to retain its operating temperature at much longer period. Moreover, solid carbon dioxide allows cryosurgical probes to be of very slim probes for very focal freezing applications.

"Skin Casing" for Solid Cold Source

A thermoconductive polyester tube, 0.55 mm thick with burst pressure of 600 psi serves as skin casing for the solid carbon dioxide. This ultra-thin material allows efficient heat transfer between the solid carbon dioxide and the tissue in contact. The nature of this material is anticipated by Mackay and Hossack. They mentioned that the "thermoconductive window" of the probe can be made up of composite metal/polymer or polymer-only (UK Patent Application #GB 2 236 253 A). The said tube extends from the tip to the handle portion of the probe as the solid carbon dioxide it contains. It is referred as the "thermal tube" in the following "Best Mode For Carrying Out The Invention".

The Parabolic Tube

The temperature of the carbon dioxide is further maintained by circulating liquid nitrogen within a parabolic shaped tube whose vertex is in contact with the base of said solid carbon dioxide. Materials for said parabolic tube is chosen among thermoconductive polyester, thin stainless steel or copper. The parabolic tube forms a continuous path for delivery and extraction of nitrogen. One end of the parabolic tube receives liquid nitrogen from high pressure chamber. The other end returns the liquid nitrogen to a low pressure chamber. Such that all the circulated nitrogen whether in the form of liquid or gas vapors are extracted. This provides complete extraction of used liquid nitrogen and allows continuous supply of "cold" liquid nitrogen.

The Insulating Tube

A polyurethane tube lined with polyethylene in the inside circumscribes portion of the of the probe not part of thermal exchange. About 25 millimeters or less from the close end tip of the probe (which is the freeze area) protrudes from the tapering end of this insulating tube. A 10 millimeter length 7 protrudes from the other end of this insulating tube. This portion is in contact with the vertex 8 of the parabolic tube.

The Handle

The handle that houses the parabolic tube provides a greater mean free path (wider area of circulation) for less vaporization of liquid nitrogen. The frictional heat (heat generated from molecular collision between nitrogen molecules and the probe's wall) absorbed by circulating liquid nitrogen in this wider diameter parabolic tube is lesser than what it will absorb when made to travel up to the tip of a much smaller diameter probe as discussed earlier.

Method for Inducing Rupture to Targeted Cells

Mannitol of volume at least 10% of the volume of the targeted tissue is injected to targeted tissue. Mannitol elevates osmotic pressure of the targeted tissue. This condition counteracts the migration of water from the targeted cells to vascular region and allows targeted cells to absorb water injected to it. Thus, enabling targeted cells to retain water for greater ice formation within. Higher osmotic pressure within targeted cells is expected to have been induced 10 minutes after the injection of mannitol. Water should then be injected 10 minutes after the injection of mannitol. Water of volume equal to at least 50% of the volume of the targeted tissue provides targeted cells with maximum amount of water. The method of bloating cells with water prior to their freezing enables the targeted tissue to be the more favorable site for ice formation. This enables targeted tissue to freeze faster than nearby tissue and vasculatures, sparing them from being frozen.

BEST MODE FOR CARRYING OUT THE INVENTION

Thermal Tube 2

Figure 1A:
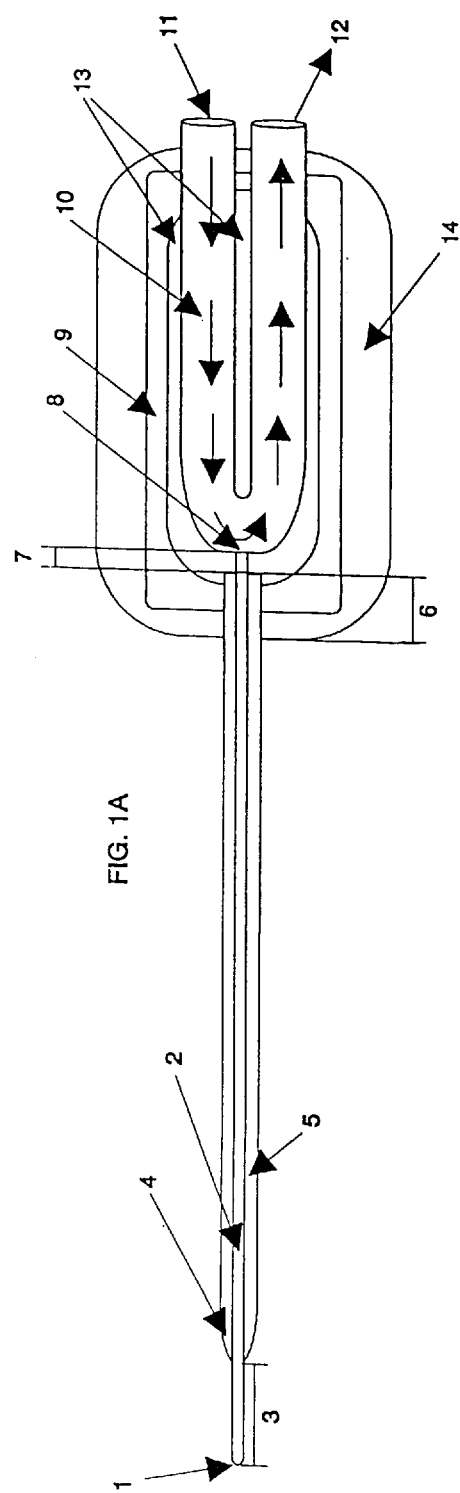
FIG. 1 is a cross-sectional view of the present probe.
Figure 2:
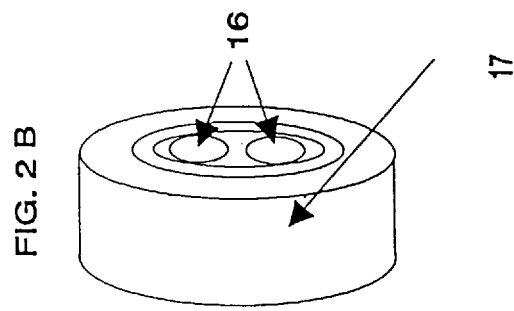
FIGS. 2A and 2B shows the outer portions of the handle.
Figure 2:
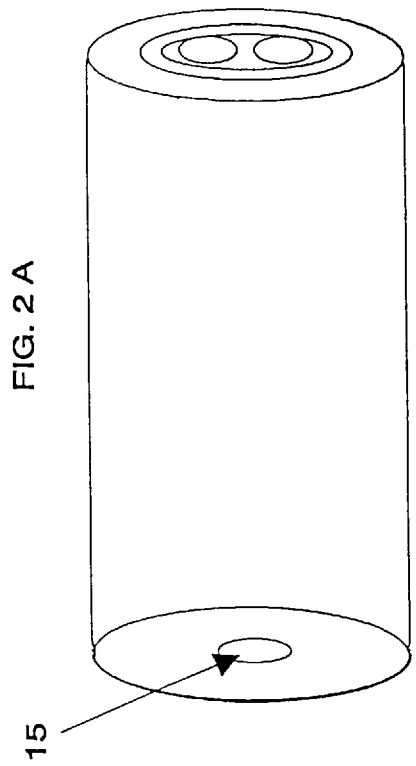
Figure 3:
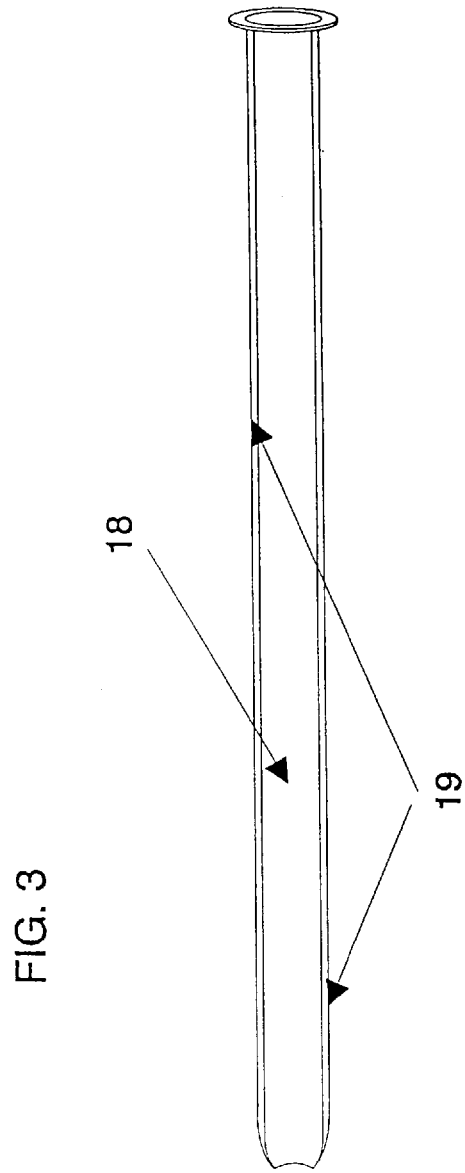
FIG. 3 shows a polyurethane canula lined with polyethylene in the inside.
Figure 4:
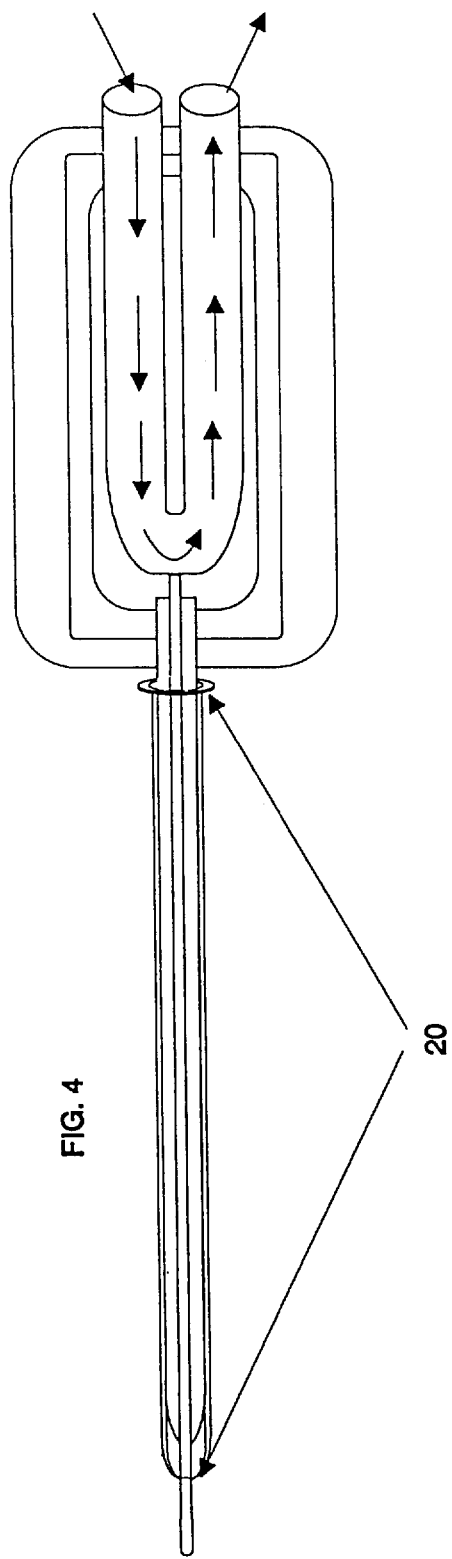
FIG. 4 shows the present cryosurgical probe inscribed in the insulating canula.
Figure 5:
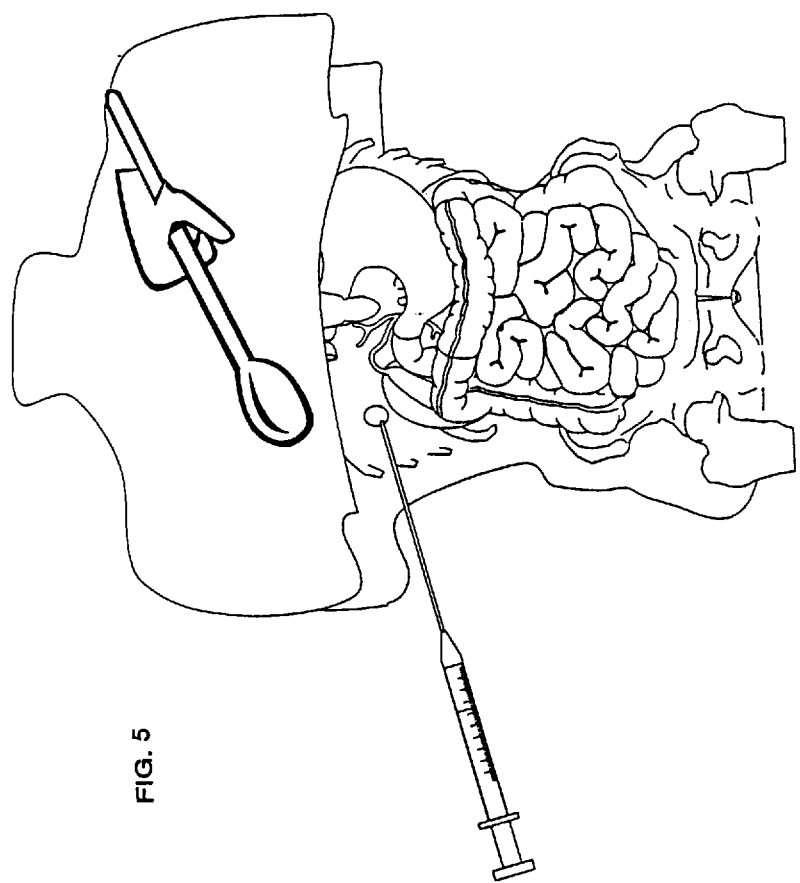
FIG. 5 shows the injection of mannitol or water to a target tissue as guided by an ultrasound probe.

The thermal tube is formed from heat shrinkable polyester plastic of 0.55 millimeter thickness and burst pressure of 600 psi. For a thermal tube of 2.5 inner diameter, a polyester sheet of length 245 millimeters and width of about 7.1 millimeters is molded to form a hollow cylinder with a close end tip and an open end of length equal to 225 millimeters.

Insulating Tube 4

For the insulating tube 4, a 12.5 millimeter width, 1.5 millimeter thickness and 195 millimeter length of rigid polyurethane plastic is molded separately to form a hollow rod of inner diameter equal to 3.6 millimeters and length of 190 millimeters.

The molded insulating tube 2 is lined with polyethylene 5. A polyethylene of 1.5 millimeter thick, 7.85 millimeter wide and 190 millimeter long is contoured and retrofitted to the insulating tube, and securely bonded within its wall by styrofoam sealant.

Parabolic Tube 10

The Parabolic Tube 10 is formed from a rigid thin polyester plastic. It is molded into hollow parabolic shaped tube 10 of 13 millimeter outer diameter, forming a 60 millimeter length from the vertex 8 to the inlet end 11 and 60 millimeter length from the vertex 8 to the outlet end 12.

Handle

The cylindrical handle, 30 millimeter inside diameter can be formed from 3 millimeter thick stainless steel, 120 millimeter length and 942.48 millimeter width. The base ends of the handle are drilled to form holes 15 and 16 of 5.51 millimeter diameter. The vacuum chamber 9 of 6 millimeters width, lining the inner walls can be formed by evacuating it to $10^{-7}$ mm Hg. by means of a molecular diffusion pump connected to a copper tube through which the space 9 is preevacuated. The copper tube is pinched off after pumping, sealing the vacuum space 9. The removable base 17 of the cylindrical handle can be formed from a circular stainless steel of 30 millimeter diameter.

Processing the Solid Cold Source

A solid carbon dioxide at −90° C. to −100° C., in the shape of a slender rod of 2.5 mm. (or less) tip diameter and 190 millimeter length is retrofitted and inscribed within the thermal tube. The thermal tube 2 containing the solid carbon dioxide is then inserted through the opening of a commercially available cryogenic cooler, having means to lower and raise samples to be cooled. The cooler is sealed to isolate it from room temperature. It is then lowered into a bath of liquid nitrogen at temperature within −200° C. to −208° C. inside the cooler. The cryogenic cooler continuously extracts evaporated nitrogen and pumps in liquid nitrogen of said temperature till the carbon dioxide reaches a temperature of −196° C. as indicated by a thermostat in contact with the unsubmerged end of the carbon dioxide.

The thermal tube 2 containing the solid carbon dioxide is then raise. It is then retrofitted to be inscribed within the insulating tube 4. About 25 millimeters from the close end tip portion of the thermoconductive tube (portion 3) protrudes from the tapering tip portion of the insulating tube 4, forming the freeze region 3 of the probe. From the other end of the insulating tube, ten millimeters (portion 7) of thermoconductive tube containing the carbon dioxide protrudes out of the free end of the insulating tube.

Assembly

The Parabolic Tube 10 is then placed inside the handle. The vertex of this parabolic tube is made to touch the protruding portion 7 of the thermal tube that contains the carbon dioxide. The rest of the space inside the handle is filled with polyethylene styrofoam, insulating the inlet and outlet portion of the parabolic tube from each other.

The inlet 11 and outlet 12 ends of the parabolic tube are then retrofitted to pass through holes 16.

Portion 6 is retrofitted to pass through hole 15 (Sheet 2). The tip of portion 7 should be placed in touch with the vertex 8 of the parabolic tube to continuously receive cold supply from circulating nitrogen within the parabolic tube 10. The inscribed portion 6 should be securely bonded to the handle by styrofoam sealant which also serves as added insulation. Immediately after a few centimeters from holes 16, the inlet 11 and outlet 12 ends of the parabolic tube are retrofitted and inscribed to a widening tubes that pump in and return liquid nitrogen to a cryogenic pump. These tubes are highly insulated, and are part of the available cryogenic pumps. An aluminum sheet of high refractive index can be wrapped around these tubes to deflect incoming radiation rays.

A seven millimeter thick elastic polyethylene styrofoam 14 is wrapped around the handle structure, forming added insulation and cushion.

This finishes up the present probe. Note that the dimensions given can be altered to form various sizes of probe.

Introduction of Mannitol/Water

Water and mannitol is injected to targeted tissue by means of a biopsy needle connected to a syringe. The biopsy needle is guided to the targeted tissue by ultrasound probe or MRI (Magnetic Resonance Imaging).

The probe is guided to the targeted tissue by the following sequential method:

1. With the biopsy needle and syringe still injected in the targeted tissue, the syringe is then pulled out to accommodate a guide wire.
2. A guide wire is inserted through the biopsy needle all the way into the targeted tissue.
3. The biopsy needle is then pulled out with the guide wire remaining.
4. A dilator in the form of a slender hollow cylinder with a tapered open tip is guided through the guide wire and into the targeted tissue and will serve to increase the diameter of insertion.
5. The insulating canula is then guided through the dilator. The dilator and guide wire is then pulled out.
6. The described probe is then inserted to the canula and into the targeted tissue with the handle portion of the probe remaining outside the canula.
7. The insulating canula remains inscribing the insulating portion of the probe, serving as an added insulation and means to adjust freeze zone 3.

We claim:

1. A cryosurgical device for freezing of tissues comprising:

a cylindrical vacuum walled handle;

a solid cold source having a length with a proximal end and a distal end, wherein an insulating tube circumscribes the length of the solid cold source with the exception of a freeze zone and a thermal heat exchange area, and further wherein the proximal end of the solid cold source including the heat exchange area is located within the handle and the distal end is adapted to contact and freeze tissue;

a thermoconductive parabolic tube located within the handle and in contact with the thermal heat exchange area of the solid cold source; and a liquid cold source connected to the parabolic tube such that the liquid cold source circulates a coolant in contact with the solid cold source to maintain the operating temperature of the solid cold source.

2. A cryosurgical device as in claim 1 wherein said solid cold source is in the shape of a slender rod that extends from the handle.

3. A cryosurgical device as in 1 wherein said solid cold source is carbon dioxide.

4. A cryosurgical device as in claim 3 wherein said carbon dioxide is at −196° C. or below.

5. A cryosurgical device as in claim 1 where said liquid cold source is liquid nitrogen.

6. A cryosurgical device as in claim 1 wherein said parabolic tube is made from a thermoconductive material chosen from the group of thermoconductive polyester, stainless steel or copper.

7. A cryosurgical device as in claim 6 wherein the vertex of the parabolic tube is in contact with the proximal end of the solid cold source at the thermal heat exchange area.

8. A cryosurgical device as in claim 6 wherein one end of the parabolic tube receives liquid nitrogen from a high pressure chamber of a liquid nitrogen storage pump, and the opposite end of the parabolic tube returns the liquid nitrogen to a low pressure chamber of the storage pump.

9. A cryosurgical device as in claim 1 wherein the insulating tube consists of polyurethane lined with polyethylene on an inside surface of the insulating tube.

10. A cryosurgical device as in claim 1 wherein the insulating tube is in the shape of a hollow rod adapted for bayonet coupling with the solid cold source, and further wherein the insulating tube tapers in proximity to the distal end of the tube.

11. A cryosurgical device as in claim 1 wherein the handle includes a distal base with an opening for bayonet coupling with the proximal portion of the insulating tube, and a proximal base which includes two openings through which an inlet and an outlet portion of said parabolic tube pass.

12. A cryosurgical device as in claim 1 and further including an insulating cannula for guiding the freeze zone of the solid cold source to tissue, the cannula including a lumen through which the solid cold source and insulating tube are inserted.

13. A cryosurgical device as in claim 12 wherein the insulating cannula is in the shape of a hollow rod with open ends, the hollow rod further being tapered toward a distal end.

14. A cryosurgical device as in claim 12 wherein the insulating cannula consists of polyurethane lined with polyethylene on an inside surface.

* * * * *